US012608900B2

(12) United States Patent (10) Patent No.: US 12,608,900 B2
Kudo et al. (45) Date of Patent: Apr. 21, 2026

(54) LEARNING APPARATUS, LEARNING METHOD, AND LEARNING PROGRAM, REGION-OF-INTEREST EXTRACTION APPARATUS, REGION-OF-INTEREST EXTRACTION METHOD, AND REGION-OF-INTEREST EXTRACTION PROGRAM, AND LEARNED EXTRACTION MODEL

(71) Applicant: FUJIFILM Corporation, Tokyo (JP)

(72) Inventors: Akira Kudo, Tokyo (JP); Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 758 days.

(21) Appl. No.: 17/578,465

(22) Filed: Jan. 19, 2022

(65) Prior Publication Data

US 2022/0139062 A1 May 5, 2022

Related U.S. Application Data

(63) Continuation of application No. PCT/JP2020/028415, filed on Jul. 22, 2020.

(30) Foreign Application Priority Data

Jul. 25, 2019 (JP) ................................. 2019-137033

(51) Int. Cl.
*G06V 10/25* (2022.01)
*A61B 6/00* (2024.01)
(Continued)

(52) U.S. Cl.
CPC ............ *G06V 10/25* (2022.01); *A61B 6/5211* (2013.01); *A61B 6/5247* (2013.01); *G06V 10/40* (2022.01);
(Continued)

(58) Field of Classification Search
CPC .............. G06V 10/25; G06V 10/7715; G06V 2201/03; G06V 10/40; A61B 6/5247; A61B 6/5211; A61B 6/03
See application file for complete search history.

(56) References Cited

U.S. PATENT DOCUMENTS

2018/0336677 A1* 11/2018 Sloan ..................... G06T 7/0012
2019/0049540 A1* 2/2019 Odry .................... G01R 33/543
(Continued)

FOREIGN PATENT DOCUMENTS

JP 2018192264 12/2018

OTHER PUBLICATIONS

Frid-Adar et al., "GAN-based Synthetic Medical Image Augmentation for increased CNN Performance in Liver Lesion Classification," arXiv, 2018, p. 1-10. (Year: 2018).*
(Continued)

*Primary Examiner* — Emily C Terrell
*Assistant Examiner* — Daniella M. DiGuglielmo
(74) *Attorney, Agent, or Firm* — JCIPRNET

(57) ABSTRACT

A learning apparatus of an extraction model that extracts a region of interest from images having a plurality of different representation formats is provided. The learning apparatus comprising one processor is configured to perform learning of an encoder, a first decoder, a first discriminator, a second decoder, and a second discriminator which constitute the extraction model. The encoder extracts a feature amount of a first image of a first representation format. The first decoder derives a second virtual image of a second representation format. The first discriminator outputs a first
(Continued)

discrimination result on a representation format of an input image and whether the input image is a real image or a virtual image. The second discriminator outputs a second discrimination result on whether an extraction result of a region of interest by the second decoder is from a first image with or without a ground-truth mask.

19 Claims, 9 Drawing Sheets

(51) Int. Cl.
<br>*A61B 6/03* (2006.01)
<br>*G06V 10/40* (2022.01)
<br>*G06V 10/77* (2022.01)

(52) U.S. Cl.
<br>CPC ............ *G06V 10/7715* (2022.01); *A61B 6/03* (2013.01); *G06V 2201/03* (2022.01)

(56) References Cited

U.S. PATENT DOCUMENTS

2019/0220977 A1* 7/2019 Zhou ...................... G06N 3/084
<br>2021/0063518 A1* 3/2021 Zhang ................... G06N 3/088

OTHER PUBLICATIONS

Ian J. Goodfellow et al., "Generative Adversarial Nets," arXiv: 1406.2661, Jun. 2014, pp. 1-9.

Judy Hoffman et al., "Cycada: Cycle-Consistent Adversarial Domain Adaptation," arXiv: 1711.03213, Dec. 2017, pp. 1-15.

Yunjey Choi et al., "StarGAN: Unified Generative Adversarial Networks for Multi-Domain Image-to-Image Translation," arXiv: 1711.09020, Sep. 2018, pp. 1-15.

"International Search Report (Form PCT/ISA/210) of PCT/JP2020/028415," mailed on Oct. 13, 2020, with English translation thereof, pp. 1-4.

"Written Opinion of the International Searching Authority (Form PCT/ISA/237)" of PCT/JP2020/028415, mailed on Oct. 13, 2020, with English translation thereof, pp. 1-6.

"Search Report of Europe Counterpart Application", issued on Aug. 29, 2022, p. 1-p. 7.

Maayan Frid-Adar et al., "GAN-based synthetic medical image augmentation for increased CNN performance in liver lesion classification," Neurocomputing, Mar. 2018, pp. 1-10.

Phillip Isola et al., "Image-to-Image Translation with Conditional Adversarial Networks," Conference: 2017 IEEE Conference on Computer Vision and Pattern Recognition (CVPR), Jul. 2017, pp. 1-16.

* cited by examiner

| INPUT | CT IMAGE | T1-WEIGHTED IMAGE | T2-WEIGHTED IMAGE |

LEARNING APPARATUS, LEARNING METHOD, AND LEARNING PROGRAM, REGION-OF-INTEREST EXTRACTION APPARATUS, REGION-OF-INTEREST EXTRACTION METHOD, AND REGION-OF-INTEREST EXTRACTION PROGRAM, AND LEARNED EXTRACTION MODEL

CROSS REFERENCE TO RELATED APPLICATIONS

The present application is a Continuation of PCT International Application No. PCT/JP2020/028415, filed on Jul. 22, 2020, which claims priority to Japanese Patent Application No. 2019-137033, filed on Jul. 25, 2019. Each application above is hereby expressly incorporated by reference, in its entirety, into the present application.

BACKGROUND

Technical Field

The present disclosure relates to a learning apparatus, a learning method, and a learning program that perform learning of an extraction model which extracts a region of interest from an image, a region-of-interest extraction apparatus, a region-of-interest extraction method, and a region-of-interest extraction program that extract a region of interest from an image, and a learned extraction model.

Related Art

Generative adversarial networks (GAN) that alternately perform learning of a generator which creates data and a discriminator which identifies data have been proposed. For example, Ian J. Goodfellow, Jean Pouget-Abadie, Mehdi Mirza, Bing Xu, David Warde-Farley, Sherjil Ozair, Aaron Courville, Yoshua Bengio "Generative Adversarial Nets", arXiv: 1406.2661 describes research on GAN. According to GAN, learning of a generative model that generates highly accurate data based on the characteristics of data for learning can be performed.

Further, Judy Hoffman, Eric Tzeng, Taesung Park, Jun-Yan Zhu, Phillip Isola, Kate Saenko, Alexei A. Efros, Trevor Darrell "CyCADA: Cycle-Consistent Adversarial Domain Adaptation", arXiv: 1711.03213 also proposes a technique of performing domain adaptation between two different domains, a source and a target. The method described in Judy Hoffman, Eric Tzeng, Taesung Park, Jun-Yan Zhu, Phillip Isola, Kate Saenko, Alexei A. Efros, Trevor Darrell "CyCADA: Cycle-Consistent Adversarial Domain Adaptation", arXiv: 1711.03213 is based on an idea that learning is performed so that feature spaces of a source image and a target image are close to each other, and with the method described in Judy Hoffman, Eric Tzeng, Taesung Park, Jun-Yan Zhu, Phillip Isola, Kate Saenko, Alexei A. Efros, Trevor Darrell "CyCADA: Cycle-Consistent Adversarial Domain Adaptation", arXiv: 1711.03213, use of a source domain with sufficient training labels enables learning of a target domain with no or few training labels with high accuracy.

Further, Yunjey Choi, Minje Choi, Munyoung Kim, Jung-Woo Ha, Sunghun Kim, Jaegul Choo "StarGAN: Unified Generative Adversarial Networks for Multi-Domain Image-to-Image Translation", arXiv: 1711.09020 proposes a network that realizes multimodal domain conversion by using a single generator and discriminator. In the method described in Yunjey Choi, Minje Choi, Munyoung Kim, Jung-Woo Ha, Sunghun Kim, Jaegul Choo "StarGAN: Unified (Ienerative Adversarial Networks for Multi-Domain Image-to-Image Translation", arXiv: 1711.09020, various facial expressions (for example, blonde hair, black hair, smiling face, angry face, and the like) in an image to be converted (for example, a person's face image) are simultaneously given to an input of the generator as domain labels, and in the discriminator, not only the authenticity of the input image but also the domain, that is, the facial expressions are determined, so that learning of the generator and the discriminator is performed.

Meanwhile, in the medical field, advances in various modalities such as a computed tomography (CT) apparatus and a magnetic resonance imaging (MRI) apparatus have made it possible to perform diagnostic imaging using a higher quality medical image. A region of interest such as an organ and a lesion included in such a medical image has also been automatically extracted. For example, a technique has been proposed in which learning of a machine learning model such as a neural network is performed by using an image for learning and a ground-truth mask of the region of interest, and the region of interest is extracted from an input image.

Incidentally, in a medical image, in a case where modalities that generate images, such as a CT apparatus and an MRI apparatus, are different from each other, image representation formats are also different from each other. For example, the density is different between a CT image and an MRI image even in a case where a tissue of a human body that is included in an image is the same. Further, the MRI image has various imaging conditions such as a T1-weighted image, a T2-weighted image, a fat-suppressed image, and a diffusion-weighted image, and the representation format differs depending on the imaging conditions. For example, on the T1-weighted image, predominantly adipose tissue appears white, water, humoral components, and cysts appear black, and tumors appear slightly black. Further, on the T2-weighted image, not only adipose tissue but also water, humoral components, and cysts appear white. Therefore, in order to extract a region of interest made to correspond to the medical images of various representation formats, it is necessary to prepare a ground-truth mask for each representation format of the medical image, that is, for each domain, and perform learning of a machine learning model. However, in a case where the ground-truth mask is prepared for each domain, a great cost is required for creating the ground-truth mask, collecting images, adjusting the parameters of the machine learning model at the time of learning, and the like. In this case, it is conceivable to apply the methods described in Judy Hoffman, Eric Tzeng, Ta.esung Park, Jun-Yan Zhu, Phillip Isola, Kate Saenko, Alexei A. Efros, Trevor Darrell "CyCADA: Cycle-Consistent Adversarial Domain Adaptation", arXiv: 1711.03213 and Yunjey Choi, Minje Choi, Munyoung Kim, Jung-Woo Ha, Sunghun Kim, Jaegul Choo "StarGAN: Unified Generative Adversarial Networks for Multi-Domain Image-to-Image Translation", arXiv: 1711.09020 to the extraction of the region of interest from the medical image.

However, the method described in Judy Hoffman, Eric Tzeng, Taesung Park, Jun-Yan Zhu, Phillip Isola, Kate Saenko, Alexei A. Efros, Trevor Darrell "CyCADA: Cycle-Consistent Adversarial Domain Adaptation", arXiv: 1711.03213 is applied only to one-to-one domain conversion of one source and one target. Therefore, in order to make the region of interest correspond to medical images having various representation formats, it is necessary to prepare a model for each combination of the domains, that is, representation formats. Further, in the method described in Yunjey Choi, Minje Choi, Munyoung Kim, Jung-Woo Ha, Sunghun Kim, Jaegul Choo "StarGAN: Unified Generative Adversarial Networks for Multi-Domain Image-to-Image Translation", arXiv: 1711.09020, the method described in Yunjey Choi, Minje Choi, Munyoung Kim, Jung-Woo Ha, Sunghun Kim, Jaegul Choo "StarGAN: Unified Generative Adversarial Networks for Multi-Domain Image-to-Image Translation", arXiv: 1711.09020 can be applied only to processing of converting an image. Furthermore, the method described in Yunjey Choi, Minje Choi, Munyoung Kim, Jung-Woo Ha, Sunghun Kim, Jaegul Choo "StarGAN: Unified Generative Adversarial Networks for Multi-Domain Image-to-Image Translation", arXiv: 1711.09020 requires a domain label for an input of a generator at the time of discrimination.

SUMMARY OF THE INVENTION

The present disclosure has been made in view of the above circumstances, and an object thereof is to make it possible to extract a region of interest that is included in a target image regardless of a representation format of the target image.

A first learning apparatus according to the present disclosure is a learning apparatus of an extraction model that extracts a region of interest from images having a plurality of different representation formats, in which the extraction model has an encoder that extracts a feature amount of a first image of a first representation format to derive a feature map of the first image, a first decoder that derives a second virtual image of a second representation format different from the representation format of the first image on the basis of the feature map, a first discriminator that discriminates a representation format of an input image and whether the input image is a real image or a virtual image generated by the first decoder, and outputs a first discrimination result, a second decoder that extracts a region of interest of the first image on the basis of the feature map, and a second discriminator that discriminates whether an extraction result of the region of interest by the second decoder is an extraction result of a first image with ground-truth mask or an extraction result of a first image without ground-truth mask, and outputs a second discrimination result, and the learning apparatus comprises a learning unit that performs learning of the encoder, the first decoder, and the first discriminator on the basis of the first discrimination result, and that performs learning of the encoder, the second decoder, and the second discriminator on the basis of the second discrimination result.

In the first learning apparatus according to the present disclosure, the learning unit may make the encoder derive a feature map of the second virtual image in response to an input of the second virtual image, make the first decoder derive a first virtual image of the first representation format on the basis of the feature map of the second virtual image, and perform learning of the encoder, the first decoder, and the first discriminator on the basis of a difference between the first image and the first virtual image.

Further, in the first learning apparatus according to the present disclosure, in a case where the first image has a ground-truth mask for the region of interest, the learning unit may perform learning of the second decoder on the basis of the extraction result of the region of interest and the ground-truth mask.

In addition, in the first learning apparatus according to the present disclosure, the extraction model may further have a third discriminator that discriminates the representation format of the first image input to the encoder on the basis of the feature map, and that outputs a third discrimination result, and the learning unit may perform learning of the encoder and the third discriminator on the basis of the third discrimination result.

A second learning apparatus according to the present disclosure is a learning apparatus of an extraction model that extracts a region of interest from images having a plurality of different representation formats, in which the extraction model has an encoder that extracts a feature amount of a first image of a first representation format to derive a feature map of the first image, a first decoder that derives a second virtual image of a second representation format different from the representation format of the first image on the basis of the feature map, a first discriminator that discriminates a representation format of an input image and whether the input image is a real image or a virtual image generated by the first decoder, and outputs a first discrimination result, a second decoder that extracts a region of interest of the first image on the basis of the feature map, and a third discriminator that discriminates the representation format of the first image input to the encoder on the basis of the feature map, and outputs a third discrimination result, and the learning apparatus comprises a learning unit that performs learning of the encoder, the first decoder, and the first discriminator on the basis of the first discrimination result, and that performs learning of the encoder and the third discriminator on the basis of the third. discrimination result.

In the first and second learning apparatuses according to the present disclosure, the image may be a three-dimensional medical image, and the representation format may include representation formats of a CT image and an MRI image.

Further, in the first and second learning apparatuses according to the present disclosure, the representation format may include at least one representation format of a T1-weighted image, a T2-weighted image, a diffusion-weighted image, a FLAIR image, a T1-weighted image before contrast enhancement, or a T1-weighted image after contrast enhancement, in an MRI image.

A region-of-interest extraction apparatus according to the present disclosure comprises an extraction unit that extracts a region of interest of an image of any representation format from the image, in which an encoder and a second decoder in an extraction model learned by the first or second learning apparatus according to the present disclosure are provided.

A learned extraction model according to the present disclosure comprises an encoder and a second decoder in an extraction model learned by the first or second learning apparatus according to the present disclosure.

A first learning method according to the present disclosure is a learning method of an extraction model that extracts a region of interest from images having a plurality of different representation formats, in which the extraction model has an encoder that extracts a feature amount of a first image of a first representation format to derive a feature map of the first image, a first decoder that derives a second virtual image of a second representation format different from the representation format of the first image on the basis of the feature map, a first discriminator that discriminates a representation format of an input image and whether the input image is a real image or a virtual image generated by the first decoder, and outputs a first discrimination result, a second decoder that extracts a region of interest of the first image on the basis of the feature map, and a second discriminator that discriminates whether an extraction result of the region of interest by the second decoder is an extraction result of a first image with ground-truth mask or an extraction result of a first image without ground-truth mask, and outputs a second discrimination result, and the learning method comprises:

performing learning of the encoder, the first decoder, and the first discriminator on the basis of the first discrimination result; and performing learning of the encoder, the second decoder, and the second, discriminator on the basis of the second discrimination result.

A second learning method according to the present disclosure is a learning method of an extraction model that extracts a region of interest from images having a plurality of different representation formats, in which the extraction model has an encoder that extracts a feature amount of a first image of a first representation format to derive a feature map of the first image, a first decoder that derives a second virtual image of a second representation format different from the representation format of the first image on the basis of the feature map, a first discriminator that discriminates a representation format of an input image and whether the input image is a real image or a virtual image generated by the first decoder, and outputs a first discrimination result, a second decoder that extracts a region of interest of the first image on the basis of the feature map, and a third discriminator that discriminates the representation format of the first image input to the encoder on the basis of the feature map, and outputs a third discrimination result, and the learning method comprises:

performing learning of the encoder, the first decoder, and the first discriminator on the basis of the first discrimination result; and performing learning of the encoder and the third discriminator on the basis of the third discrimination result.

A region-of-interest extraction method according to the present disclosure comprises extracting a region of interest of an image of any representation format from the image, in which an encoder and a second decoder in an extraction model learned by the first or second learning method according to the present disclosure are provided.

The first and second learning methods and the region-of-interest extraction method. according to the present disclosure may be provided as programs to be executed by a computer.

A third learning apparatus according to the present disclosure is a learning apparatus of an extraction model that extracts a region of interest from images having a plurality of different representation formats, the learning apparatus comprising:

a memory that stores a command to be executed by a computer; and a processor configured to execute the stored command, in which the extraction model has an encoder that extracts a feature amount of a first image of a first representation format to derive a feature map of the first image, a first decoder that derives a second virtual image of a second representation format different from the representation format of the first image on the basis of the feature map, a first discriminator that discriminates a representation format of an input image and whether the input image is a real image or a virtual image generated by the first decoder, and outputs a first discrimination result, a second decoder that extracts a region of interest of the first image on the basis of the feature map, and a second discriminator that discriminates whether an extraction result of the region of interest by the second decoder is an extraction result of a first image with ground-truth mask or an extraction result of a first image without ground-truth mask, and outputs a second discrimination result, and the processor executes a process including performing learning of the encoder, the first decoder, and the first discriminator on the basis of the first discrimination result, and performing learning of the encoder, the second decoder, and the second discriminator on the basis of the second discrimination result.

A fourth learning apparatus according to the present disclosure is a learning apparatus of an extraction model that extracts a region of interest from images having a plurality of different representation formats, the learning apparatus comprising:

a memory that stores a command to be executed by a computer; and a processor configured to execute the stored command, in which the extraction model has an encoder that extracts a feature amount of a first image of a first representation format to derive a feature map of the first image, a first decoder that derives a second virtual image of a second representation format different from the representation format of the first image on the basis of the feature map, a first discriminator that discriminates a representation format of an input image and whether the input image is a real image or a virtual image generated by the first decoder, and outputs a first discrimination result, a second decoder that extracts a region of interest of the first image on the basis of the feature map; and a third discriminator that discriminates the representation format of the first image input to the encoder on the basis of the feature map, and outputs a third discrimination result, and the processor executes a process including performing learning of the encoder, the first decoder, and the first discriminator on the basis of the first discrimination result, and performing learning of the encoder and the third discriminator on the basis of the third discrimination result.

Another region-of-interest extraction apparatus according to the present disclosure comprises: a memory that stores a command to be executed by a computer; and a processor configured to execute the stored command, in which the processor executes a process including functioning as an encoder and a second decoder in an extraction model learned by the first or second learning method according to the present disclosure, and extracting a region of interest of an image of any representation format from the image.

According to the present disclosure, a region of interest included in a target image can be extracted regardless of a representation format of the target image.

DETAILED DESCRIPTION

Figure 1:
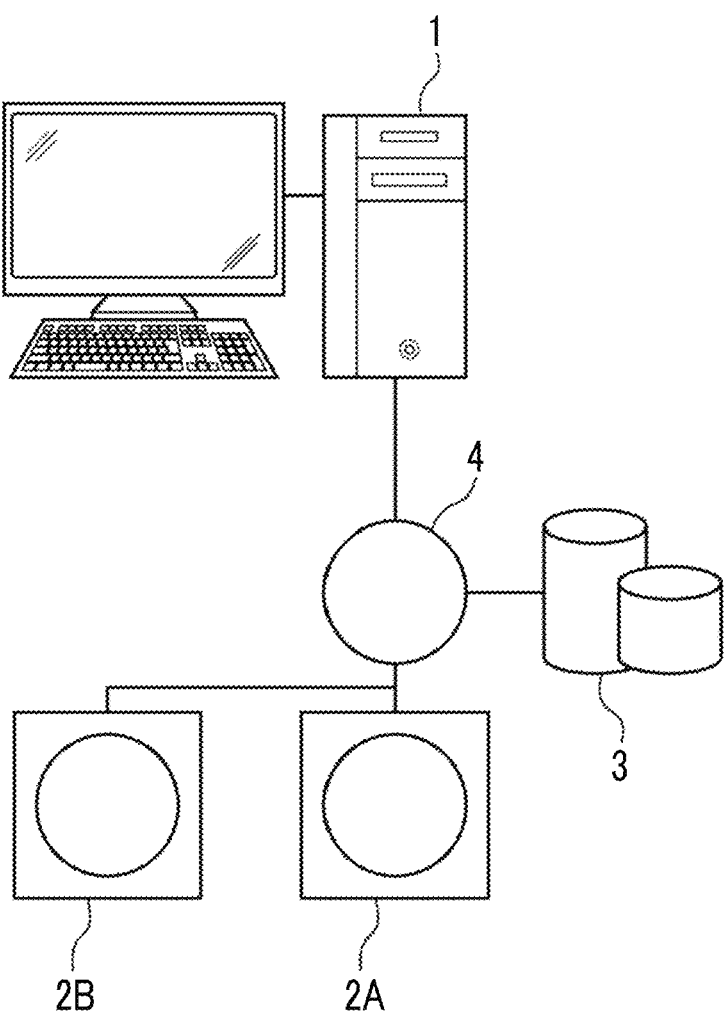
FIG. 1 is a hardware configuration diagram showing an outline of a diagnosis support system to which a learning apparatus and a region-of-interest extraction apparatus according to a first embodiment of the present disclosure are applied.

Hereinafter, embodiments of the present disclosure will be described with reference to the drawings. FIG. 1 is a hardware configuration diagram showing an outline of a diagnosis support system to which a learning apparatus and a region-of-interest extraction apparatus according to a first embodiment of the present disclosure are applied, As shown in FIG. 1, in the diagnosis support system, a learning apparatus and region-of-interest extraction apparatus (hereinafter, represented by a region-of-interest extraction apparatus) 1, a plurality of three-dimensional image capturing apparatuses 2A and 2B, and an image storage server 3 according to the first embodiment are connected to communicate with one another via a network 4.

The three-dimensional image capturing apparatuses 2A and 2B are apparatuses each of which images an area to be diagnosed of a subject and generates a three-dimensional image representing the area, and specific examples thereof include a CT apparatus, an MRI apparatus, and a positron emission tomography (PET) apparatus. The three-dimensional images generated by the three-dimensional image capturing apparatuses 2A and 213 are transmitted to and stored on the image storage server 3. In the present embodiment, the three-dimensional image capturing apparatus 2A is a CT apparatus, and the three-dimensional image capturing apparatus 2B is an MRI apparatus, and the three-dimensional image capturing apparatuses 2A and 2B generate a CT image and an MRI image including the area to be diagnosed of the subject, as a three-dimensional image, respectively. Further, in the present embodiment, the three-dimensional image capturing apparatus 2B generates a T1-weighted image and a T2-weighted image, as an MRI image. The three-dimensional image consists of a plurality of tomographic images. Further, in the present embodiment, the three-dimensional image is acquired in a case where the abdomen of the subject is imaged, and the liver included in the abdomen is a region of interest to be extracted.

Here, in a medical image, in a case where modalities that are acquired, such as a CT apparatus and an MRI apparatus, are different from each other, image representation formats are also different from each other. For example, the density is different between a CT image and an MRI image even in a case where a tissue of a human body that is included in an image is the same. Further, representation formats are different between the T1-weighted image and the T2-weighted image even in a case where the same MRI image is used. Specifically, on the T1-weighted image, predominantly adipose tissue appears white, water, humoral components, and cysts appear black, and tumors appear slightly black. Further, on the T2-weighted image, not only adipose tissue but also water, humoral components, and cysts appear white. Therefore, the CT image, the T1-weighted image, and the T2-weighted image are images having different representation formats from each other. In the present embodiment, the representation format corresponds to a domain, and different representation formats are synonymous with different domains.

The image storage server 3 is a computer that stores and manages various data and comprises a large-capacity external storage device and database management software. The image storage server 3 communicates with another apparatus via a wired or wireless network 4 to transmit and receive image data and the like. Specifically, the image storage server 3 acquires various data including the image data of the three-dimensional image generated by the three-dimensional image capturing apparatus 2 via the network, and stores and manages the acquired data on a recording medium such as a large-capacity external storage device. A storage format of the image data and the communication between the apparatuses via the network 4 are based on a protocol such as digital imaging and communication in medicine (DICOM). Further, in the present embodiment, the image storage server 3 also stores and manages an image for learning that is used to perform learning of an extraction model, which will be described later.

The region-of-interest extraction apparatus 1 including the learning apparatus of the present embodiment is an apparatus in which a learning program and a region-of-interest extraction program of the first embodiment are installed on one computer. The computer may be a workstation or a personal computer directly operated by a doctor who makes diagnosis, or may be a server computer connected to the workstation or the personal computer via a network. The learning program and the region-of-interest extraction program are stored on a storage device of a server computer connected to the network or on network storage so as to be accessible from the outside, and are downloaded and installed on a computer that the doctor uses according to a request. Alternatively, the learning program and the region-of-interest extraction program are recorded on a recording medium, such as a digital versatile disc (DVD) or a compact disc read only memory (CD-ROM), and are distributed and installed on a computer from the recording medium.

Figure 2:
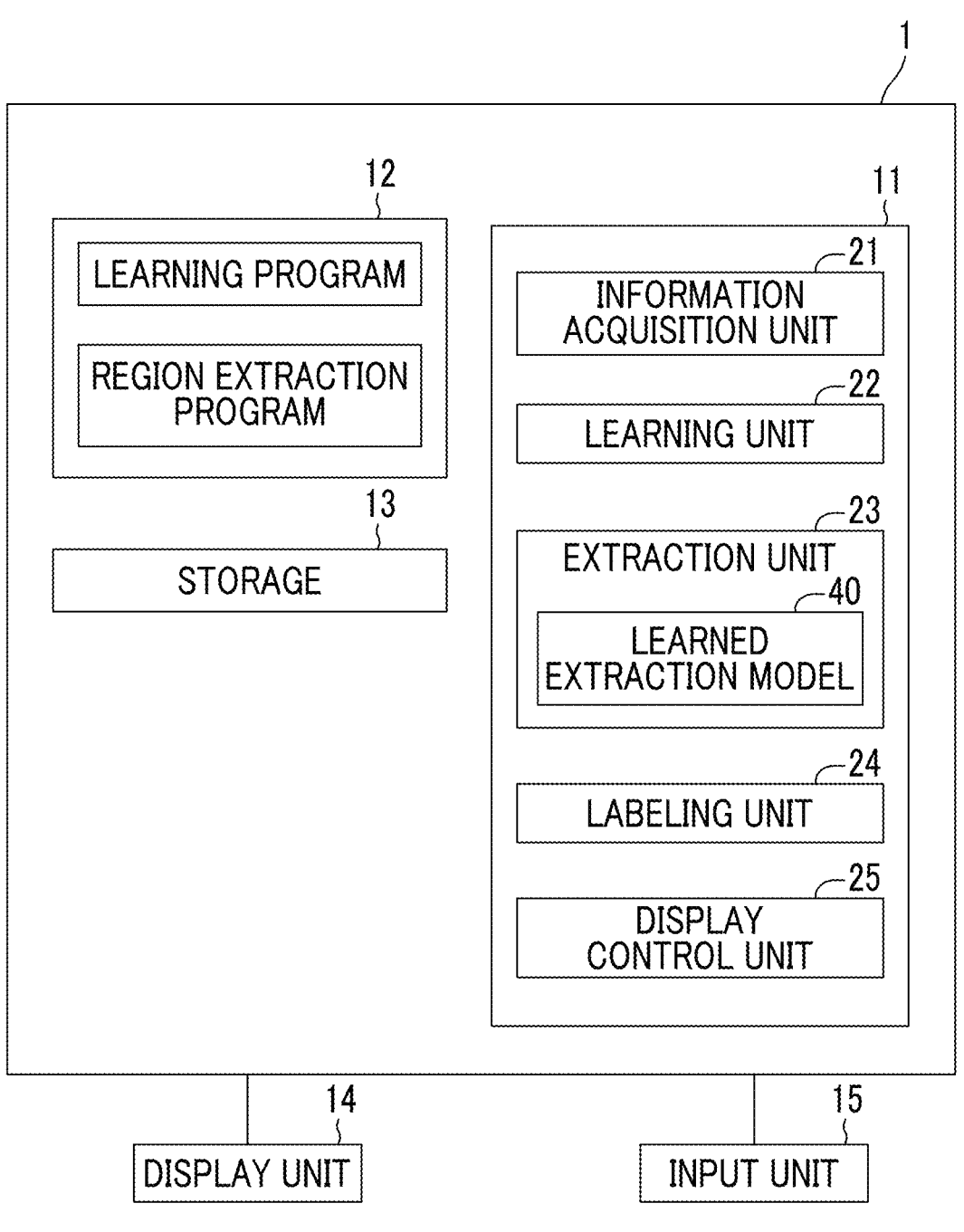
FIG. 2 is a diagram showing a schematic configuration of the region-of-interest extraction apparatus according to the first embodiment of the present disclosure.

FIG. 2 is a diagram showing a schematic configuration of the region-of-interest extraction apparatus which is realized with the learning program and the region-of-interest extraction program installed on a computer. As shown in FIG. 2, the region-of-interest extraction apparatus 1 comprises a central processing unit (CPU) 11, a memory 12, and a storage 13, as a standard workstation configuration. Further, a display unit 14, such as a liquid crystal display, and an input unit 15, such as a keyboard and a mouse, are connected to the region-of-interest extraction apparatus 1.

The storage 13 includes a hard disk drive or the like, and stores a target image as a region-of-interest extraction target, which is acquired from the image storage server 3 via the network 4, an image for learning that is used to perform learning of an extraction model 30, which will be described later, and various information including information required for processing.

Further, the learning program and the region-of-interest extraction program are stored on the memory 12. As processing to be executed by the CPU 11, the learning program defines information acquisition processing of acquiring an image for learning that is used to perform learning of an extraction model, a target image as a region-of-interest extraction target, and various information that is used to perform learning and extract a region of interest, and learning processing of performing learning of the extraction model.

As processing to be executed by the CPU 11, the region-of-interest extraction program defines extraction processing of extracting a region of interest included in the target image as a region-of-interest extraction target, which is acquired by the information acquisition processing, labeling processing of labeling the region of interest included in the target image according to an extraction result of the region of interest, and display control processing of displaying the labeled target image on the display unit 14.

The CPU 11 executes the processing in accordance with the learning program and the region-of-interest extraction program, so that the computer functions as an information acquisition unit 21, a learning unit 22, an extraction unit 23, a labeling unit 24, and a display control unit 25.

The information acquisition unit 21 acquires, as the target image, a three-dimensional image of the abdomen of the subject, from the image storage server 3 via an interface (not shown) connected to the network. The information acquisition unit 21 also acquires an image for learning and a ground-truth mask, which will be described later. Further, the information acquisition unit 21 acquires various information that is used to perform learning by the learning unit 22. The information that is used to perform learning is, for example, information on the representation format after conversion of the image for learning (that is, the target), which will be described later.

Figure 3:
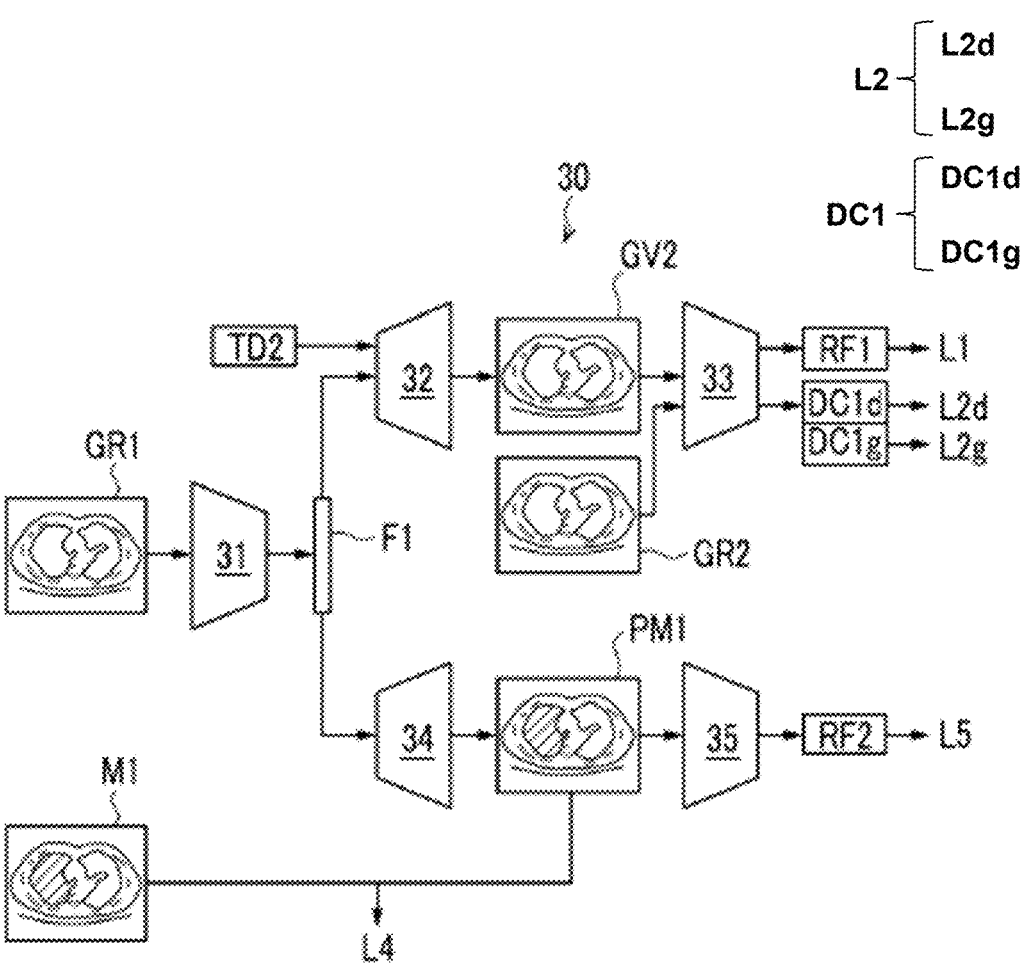
FIG. 3 is a schematic block diagram showing a configuration of an extraction model according to the first embodiment.
Figure 4:
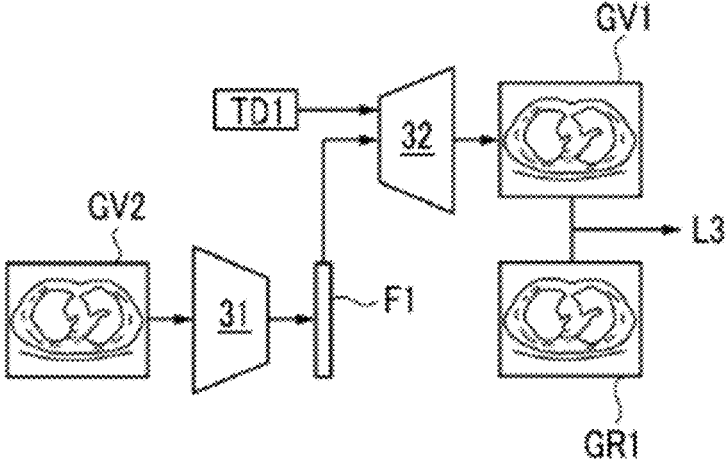
FIG. 4 is a schematic block diagram showing a configuration of the extraction model according to the first embodiment.

The learning unit 22 performs learning of an extraction model that extracts a region of interest from images having a plurality of different representation formats. FIGS. 3 and 4 are schematic block diagrams showing the configuration of the extraction model according to the first embodiment. As shown in FIGS. 3 and 4, the extraction model 30 has an encoder 31, a first decoder 32, a first discriminator 33, a second decoder 34, and a second discriminator 35. The encoder 31, the first decoder 32, and the first discriminator 33 included in the extraction model 30 constitute a domain conversion network that is used to convert the representation format of an input image, that is, convert the domain. Further, the encoder 31, the second decoder 34, and the second discriminator 35 included in the extraction model 30 constitute a region extraction network that is used to extract a region of interest from the input image. In the present embodiment, the encoder 31 is shared in the domain conversion network and the region extraction network.

In the present embodiment, the domain conversion network constitutes generative adversarial networks (GAN). The GAN comprises a "generator" that creates data and a "discriminator" that identifies data. In the present embodiment, the combination of the encoder 31 and the first decoder 32 corresponds to the generator, and the first discriminator 33 corresponds to the discriminator.

Further, in the present embodiment, the region extraction network also constitutes generative adversarial networks, and the combination of the encoder 31 and the second decoder 34 corresponds to the generator, and the second discriminator 35 corresponds to the discriminator.

The encoder 31 consists of a convolutional neural network (CNN), which is one of multi-layer neural networks in which a plurality of processing layers are hierarchically connected, and derives a feature map representing a feature amount of an input image. Specifically, as shown in FIG. 3, in a case where a first image GR1 of a first representation format is input, the encoder 31 derives a feature map F1 representing the feature amount of the first image GR1. In the present embodiment, the first image GRI is an actual image (real image) generated by the three-dimensional image capturing apparatuses 2A and 2B.

A convolutional neural network consists of a plurality of convolutional layers. The convolutional layer performs convolution processing using various kernels on an image that is input, and outputs a feature map consisting of feature amount data obtained by the convolution processing. In the present embodiment, the number of channels of the first convolutional layer (that is, the input layer) is 48 or more, but the number is not limited thereto. The kernel has an n×n pixel size (for example, n=3), and each element is weighted. Specifically, weight such as a differential filter by which the edge of the input image is weighted is set. The convolutional layer applies the kernel to the entire input image or feature map output from the previous processing layer, while shilling the pixel of interest of the kernel. Furthermore, the convolutional layer applies an activation function such as a sigmoid function to the convolution value, and outputs a feature map F1. In the present embodiment, since the convolutional neural network does not have a pooling layer, the kernel is applied to the input image or feature map while being shifted by two or more strides during the convolution processing.

Figure 5:
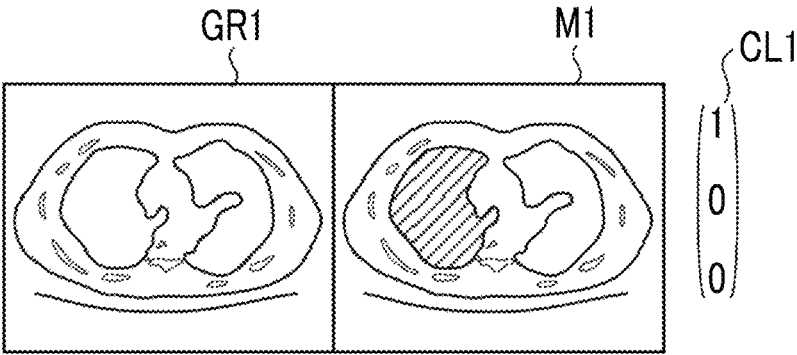
FIG. 5 is a diagram showing an example of a first image having a ground-truth mask.
Figure 6:
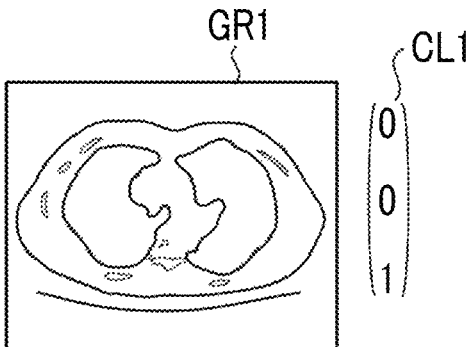
FIG. 6 is a diagram showing an example of a first image having no ground-truth mask.

Here, in the present embodiment, a plurality of types of images having different representation formats, that is, different domains, such as a CT image, a T1-weighted image, and a T2-weighted image, are used for learning of the extraction model 30. At the time of learning, a label indicating the representation format is given to the image that is input, as a class label. For example, the first image GR1 shown in FIG. 3 is given a class label indicating a representation format class of the first image GR1. In addition, the images that are used at the time of learning are prepared with and without a ground-truth mask. FIG. 5 is a diagram showing an example of the first image GR1 having a ground-truth mask M1, and FIG. 6 is a diagram showing an example of the first image GR1 having no ground-truth mask. The first image GRI shown in FIGS. 5 and 6 is given a class label CL1.

In the present embodiment, the class label CL1 is a vector having three elements that are used to identify the classes of the three representation formats, and the element to which 1 is assigned indicates the representation format of the image. In FIGS. 5 and 6, the three elements indicate a CT image, a T1-weighted image, and a T2-weighted image from the top. In the first image GRI shown in FIG. 5, since 1 is assigned to the uppermost element of the class label CL1, the representation format is a CT image. Further, in the first image GR1 shown in FIG. 6, since 1 is assigned to the third element of the class label, the representation format is a T2-weighted image. In the present embodiment, the representation format given to the image that is input is denoted by a first representation format.

The first decoder 32 converts the first representation format of the input image into a second representation format different from the first representation format on the basis of the feature map, to derive a virtual image. That is, as shown in FIG. 3, in a case where the feature map F1 of the first image GR1 is input, the first decoder 32 converts the first representation format of the first image GR1 into a second representation format different from the first representation format, to derive a second virtual image GV2. The first representation format corresponds to the source domain that is the conversion source, and the second representation format corresponds to the target domain that is the conversion destination. For this reason, information TD2 on the target domain, which is the second representation format, is input to the first decoder 32. The second representation format is input from, for example, the input unit 15. The information TD2 on the second representation format is a vector indicating the class label of the second representation format, and has the same three elements as in the class label CL1.

The first decoder 32 has a plurality of deconvolutional layers. The deconvolutional layer performs the same processing as the convolutional layer of the encoder 31, but applies the kernel for the deconvolution operation to the feature map while upsampling the input feature map. Specifically, as shown in FIG. 3, the first decoder 32 performs processing of converting the representation format of the first image GR1 into the second representation format while increasing the resolution of the feature map F1 output by the encoder 31 to the resolution of the first image GR1, to derive the second virtual image GV2 of the second representation format.

The first discriminator 33 consists of, for example, a convolutional neural network, and discriminates the representation format of the input image and whether the input image is a real image or a virtual image generated by the first decoder 32, and outputs a first discrimination result. The first discrimination result includes a discrimination result RF1 as to whether the input image is a real image or a virtual image. Further, the first discrimination result includes a discrimination result DC1 on the representation format of the input image. Here, the real image is not an image generated by the first decoder 32 but an image generated by the three-dimensional image capturing apparatuses 2A and 2B, so to speak, a genuine image.

Therefore, in a case where the first discriminator 33 discriminates that the input real image is a real image, the discrimination result RF1 is correct, and in a case where the first discriminator 33 discriminates that the input real image is a virtual image, the discrimination result RF1 is incorrect. Alternatively, in a case where the first discriminator 33 discriminates that the input virtual image is a real image, the discrimination result RF1 is incorrect, and in a case where the first discriminator 33 discriminates that the input virtual image is a virtual image, the discrimination result RF1 is correct. In the present embodiment, as shown in FIG. 3, in a case where the second virtual image GV2 is input to the first discriminator 33 at the time of learning, if the discrimination result RF1 is a virtual image, the discrimination result RF1 is correct, and if the discrimination result is a real image, the discrimination result RF1 is incorrect. Further, as shown in FIG. 3, in a case where a second image GR2 which is a real image is input to the first discriminator 33 at the time of learning, if the discrimination result RF1 is a real image, the discrimination result RF1 is correct, and if the discrimination result is a virtual image, the discrimination result RF1 is incorrect.

The learning unit 22 derives a loss on the basis of the discrimination result RF1 output by the first discriminator 33. The loss is referred to as an adversarial loss. In the present embodiment, the adversarial loss in the first discriminator 33 is denoted by a first loss Further, in a case where the representation format of the input image is a CT image, if the first discriminator 33 discriminates that the representation format is a CT image, the discrimination result DC1 is correct, and if the first discriminator 33 discriminates that the representation format is an image other than the CT image, the discrimination result DC1 is incorrect. Alternatively, in a case where the representation format of the input image is a T2-weighted image, if the first discriminator 33 discriminates that the representation format is a T2-weighted image, the discrimination result DC1 is correct, and if the first discriminator 33 discriminates that the representation format is an image other than the T2-weighted image, the discrimination result DC1 is incorrect. In the present embodiment, in a case where learning of the first discriminator 33 for making the first discriminator 33 output the discrimination result DC1 is performed, the second image GR2, which is a real image, is input to the first discriminator 33.

On the other hand, in the present embodiment, in order to perform learning of the encoder 31 and the first decoder 32 as described later, the virtual image derived by the first decoder 32 is input to the first discriminator 33, and the discrimination result DC1 is output. For example, in the present embodiment, the second virtual image GV2 is generated by using the T2-weighted image as the second representation format. Therefore, in a case where the second virtual image GV2 which is a T2-weighted image is input to the first discriminator 33, if the discrimination result DC1 is a T2-weighted image, the discrimination result DC1 is correct and if the discrimination result DC1 is a CT image or T1-weighted image other than the T2-weighted image, the discrimination result DC1 is incorrect. In the following description, in order to perform learning of the first discriminator 33, the discrimination result DC1 output from the first discriminator 33 is referred to as a discrimination result DC1$d$, and in order to perform learning of the encoder 31 and the first decoder 32, the discrimination result DC1 output from the first discriminator 33 is referred to as a discrimination result DC1$g$.

The learning unit 22 derives losses on the basis of the discrimination results DC1$d$ and DC1$g$ output by the first discriminator 33. The loss is referred to as a classification loss. In the present embodiment, the classification losses derived on the basis of the discrimination results DC1$d$ and DC1$g$ are denoted by second losses L2$d$ and L2$g$, respectively. In the following description, the discrimination results DC1$d$ and DC1$g$ may be represented by the discrimination result DC1, and the second losses L2$d$ and L2$g$ may be represented by the second loss L2.

Meanwhile, in the present embodiment, as shown in FIG. 4, the second virtual image GV2 is input to the encoder 31, the feature map F1 derived by the encoder 31 is input to the first decoder 32, and information TD1 on the first representation format of the first image GR1 is further input to the first decoder 32. With this, the first decoder 32 derives a first virtual image GV1. It is desirable that the first virtual image GV1 derived in this way completely matches the first image GR1, but there is a difference between the first virtual image GV1 that has been subjected to processing by the encoder 31 and the first decoder 32 and the first image GR1. In the present embodiment, the learning unit 22 derives the difference between the first virtual image GV1 and the first image GR1, as a loss. The loss is referred to as a cycle loss. In the present embodiment, the cycle loss is denoted by a third loss L3.

In the present embodiment, the learning unit 22 performs learning of the first discriminator 33 so that the first discriminator 33 correctly discriminates the discrimination result RF1 as to whether the input image is a real image or a virtual image generated by the first decoder 32 and correctly discriminates the discrimination result DC1$d$ on the representation format of the input image. That is, learning of the first discriminator 33 is performed so that the first loss L1 is maximized and the second loss L2$d$ is minimized. Specifically, learning of the first discriminator 33 is performed so that $-$L1$+$L2$d$ is a predetermined threshold value or less.

Further, the learning unit 22 performs learning of the first decoder 32 so that the first decoder 32 derives a virtual image of the representation format designated from the input image, for which the first discriminator 33 incorrectly discriminates the discrimination result RF1 and correctly discriminates the discrimination result DC1$g$. Further, the learning unit 22 performs learning of the encoder 31 so that the encoder 31 derives the feature map F1 from which a virtual image for which the first discriminator 33 incorrectly discriminates the discrimination result RF1 and correctly discriminates the discrimination result DC1 can be generated. That is, learning of the encoder 31 and the first decoder 32 is performed so that the first loss L1 and the second loss L2$g$ are minimized. Specifically, learning of the encoder 31 and the first decoder 32 is performed so that L1$+$L2$g$ is a predetermined threshold value or less.

Further, the learning unit 22 performs learning of the first decoder 32 so that the first virtual image GV1 generated from the second virtual image GV2 matches the first image GR1. Further, the learning unit 22 performs learning of the encoder 31 so that the encoder 31 derives the feature map F1 from which the first decoder 32 can derive the first virtual image GV1 that matches the first image GR1. That is, learning of the encoder 31 and the first decoder 32 is performed so that the third loss L3 is minimized. Specifically, learning of the encoder 31 and the first decoder 32 is performed so that L3 is a predetermined threshold value or less.

As the learning progresses, the encoder 31 and the first decoder 32, and the first discriminator 33 improve the accuracy thereof with each other, and the first discriminator 33 can more accurately discriminate a real image or a virtual image even in a case where an image of any representation format is input. On the other hand, the encoder 31 and the first decoder 32 can generate a virtual image closer to a genuine representation format image, which is not discriminated by the first discriminator 33.

Figure 7:
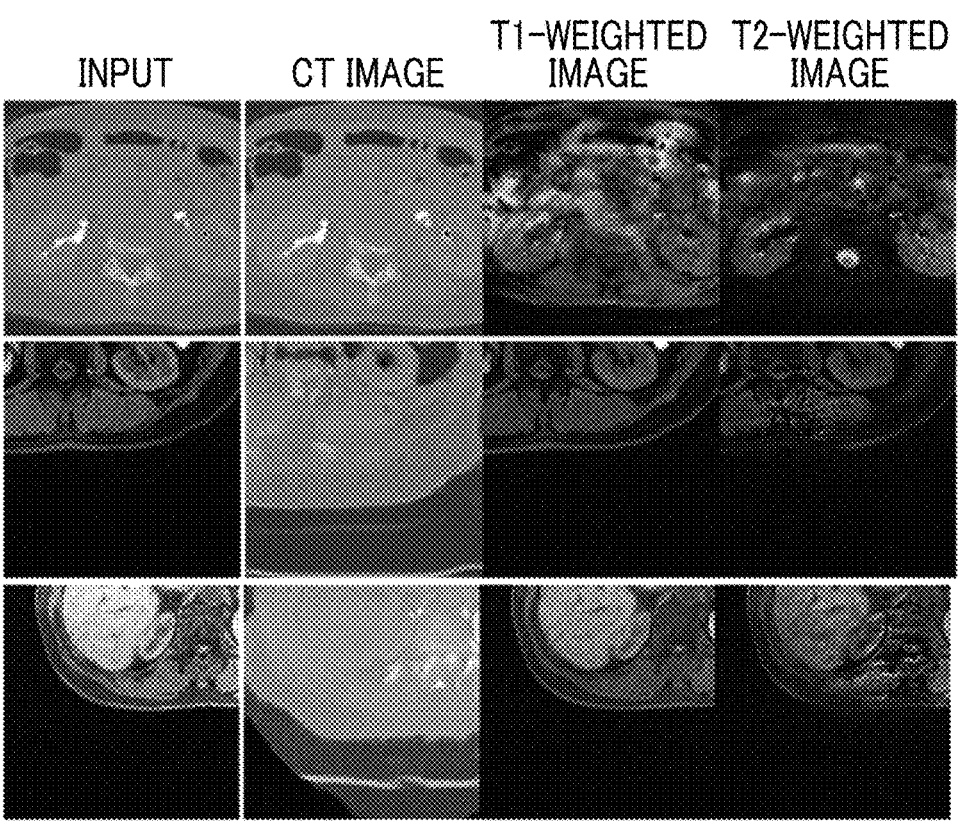
FIG. 7 is a diagram showing representation formats of real images that are input and representation formats of converted virtual images.

FIG. 7 is a diagram showing representation formats of real images that are input and. representation formats of converted virtual images. In FIG. 7, the leftmost column is the real images that are input, and the representation formats are a CT image, a T1-weighted image, and a T2-weighted image in order from the second column on the left side. Further, the virtual images of the converted representation formats are shown from the second to fourth columns on the left side. The representation formats are a CT image, a T1-weighted image, and a T2-weighted image, in order from the second column on the left side. According to the present embodiment, as shown in FIG. 7, a virtual image close to a representation format as instructed is generated regardless of the representation format of the real image that is input.

Meanwhile, the second decoder 34 extracts a region of interest of the image input to the encoder 31 by using the feature map derived by the encoder 31. Specifically, as shown in FIG. 3, the second decoder 34 extracts the region of interest of the first image GR1 by using the feature map F1 of the first image GR1. The second decoder 34 consists of a convolutional neural network having a plurality of deconvolutional layers. The second decoder 34 performs processing of deriving the probability of being the region of interest included in the first image GR1 (liver in the present embodiment), and extracting a pixel in which the probability is a threshold value or more, as the region of interest, while increasing the resolution of the feature map F1 output by the encoder 31 to the resolution of the first image GR1. As a result, as shown in FIG. 3, the second decoder 34 outputs an extraction result PM1 of a liver in the first image GR1.

In a case where the first image GR1 has a ground-truth mask M1, as shown in FIG. 3, the learning unit 22 derives a difference between the extraction result PM1 of the region of interest output by the second decoder 34 and the ground-truth mask M1, as a loss. The loss is referred to as a task loss. In the present embodiment, the task loss is denoted by a fourth loss L4.

The second discriminator 35 consists of, for example, a convolutional neural network, and discriminates whether the extraction result PM1 of the region of interest by the second decoder 34 is an extraction result of the first image GR1 with the ground-truth mask M1 as shown in FIG. 5 or an extraction result of the first image GR1 without the ground-truth mask as shown in FIG. 6, and outputs a second discrimination result RF2. Here, as shown in FIG. 3, in a case where the extraction result PM1 for the first image GR1 having the ground-truth mask M1 is input, if the second discriminator 35 discriminates the first image GR1 with the ground-truth mask, the second discrimination result RF2 is correct, and if the second discriminator 35 discriminates the first image GR1 without the ground-truth mask, the second discrimination result RF2 is incorrect. On the other hand, in a case where the extraction result PMI for the first image GR1 having no ground-truth mask M1 is input, if the second discriminator 35 discriminates the first image GR1 with the ground-truth mask, the second discrimination result RF2 is incorrect, and if the second discriminator 35 discriminates the first image GR1 without the ground-truth mask, the second discrimination result RF2 is correct. The learning unit 22 derives a loss on the basis of the output of the second discriminator 35 with regard to the second discrimination result RF2. The loss is referred to as an adversarial loss. In the present embodiment, the adversarial loss in the second discriminator 35 is denoted by a fifth loss L5.

In the present embodiment, the learning unit 22 performs learning of the second discriminator 35 so that the second discriminator 35 correctly discriminates the second discrimination result RF2 as to whether the extraction result is the extraction result of the first image GR1 with the ground-truth mask or the extraction result of the first image GR1 without the ground-truth mask. That is, learning of the second discriminator 35 is performed so that the fifth loss L5 is maximized. Specifically, learning of the second discriminator 35 is performed so that −L5 is a predetermined threshold value or less.

In the present embodiment, at the time of learning, learning is performed by alternately using the first image GR1 with the ground-truth mask and the first image GR1 without the ground-truth mask.

Further, the learning unit 22 performs learning of the second decoder 34 so that the extraction result M1 matches the ground-truth mask M1 in a case where the feature map F1 of the first image GR1 with the ground-truth mask M1 is input. Further, the learning unit 22 performs learning of the encoder 31 so that the encoder 31 derives the feature map F1 from which the extraction result PM1 that matches the ground-truth mask M1 can be obtained. That is, learning of the encoder 31 and the second decoder 34 is performed so that the fourth loss L4 is minimized. Specifically, learning of the encoder 31 and the second decoder 34 is performed so that L4 is a predetermined threshold value or less.

Further, the learning unit 22 performs learning of the second decoder 34 so that second decoder 34 outputs the extraction result PM1 for which the second discriminator 35 incorrectly discriminates the second discrimination result RF2. Further, the learning unit 22 performs learning of the encoder 31 so that the encoder 31 derives the feature map F1 from which the extraction result PM1 for which the second discriminator 35 incorrectly discriminates the second discrimination result RF2 is output. That is, learning of the encoder 31 and the first decoder 32 is performed so that the fifth loss L5 is minimized. Specifically, learning of the encoder 31 and the first decoder 32 is performed so that L5 is a predetermined threshold value or less.

As the learning progresses, the encoder 31 and the first decoder 32, and the first discriminator 33 improve the accuracy thereof with each other, and the second discriminator 35 can more accurately discriminate whether the input image has the ground-truth mask or no ground-truth mask. On the other hand, the encoder 31 and the second decoder 34 can output the more accurate extraction result of the region of interest, in which the presence or absence of the ground-truth mask is not discriminated by the second discriminator 35, regardless of the image with or without the ground-truth mask.

With learning of the extraction model 30 performed by the learning unit 22 as described above, in a case where the target image as a region-of-interest extraction target is input, the extraction model 30 that extracts a region of interest included in the target image is constructed regardless of the representation format of the target image. In the present embodiment, the encoder 31 and the second decoder 34 in the extraction model 30 that has been learned are applied to the extraction unit 23 as a learned extraction model 40.

In a case where the target image is input, the extraction unit 23 extracts the region of interest included in the target image by using the learned extraction model 40 and outputs the extraction result.

The labeling unit 24 labels the region of interest included in the target image on the basis of the extraction result of the region of interest output by the extraction unit 23.

Figure 8:
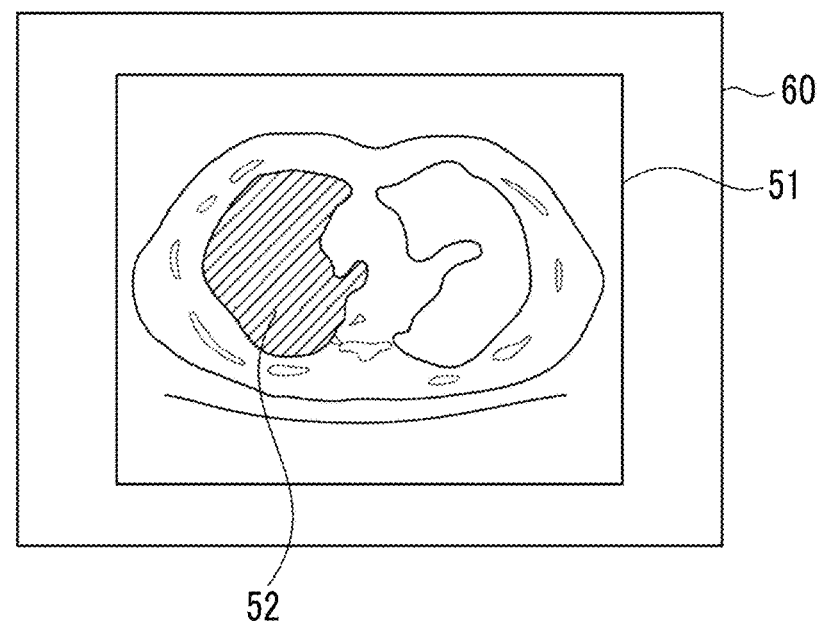
FIG. 8 is a diagram showing a labeled target image.

The display control unit 25 displays the labeled target image on the display unit 14. FIG. 8 is a diagram showing a display screen of the labeled target image. As shown in FIG. 8, the target image 51 is displayed on the display screen 60, and labeling 52 is performed on the region of interest in the target image 51. Although hatching is used for the labeling 52 shown in FIG. 8, the labeling may be performed by changing color, surrounding the region of interest with a line, or the like.

Figure 9:
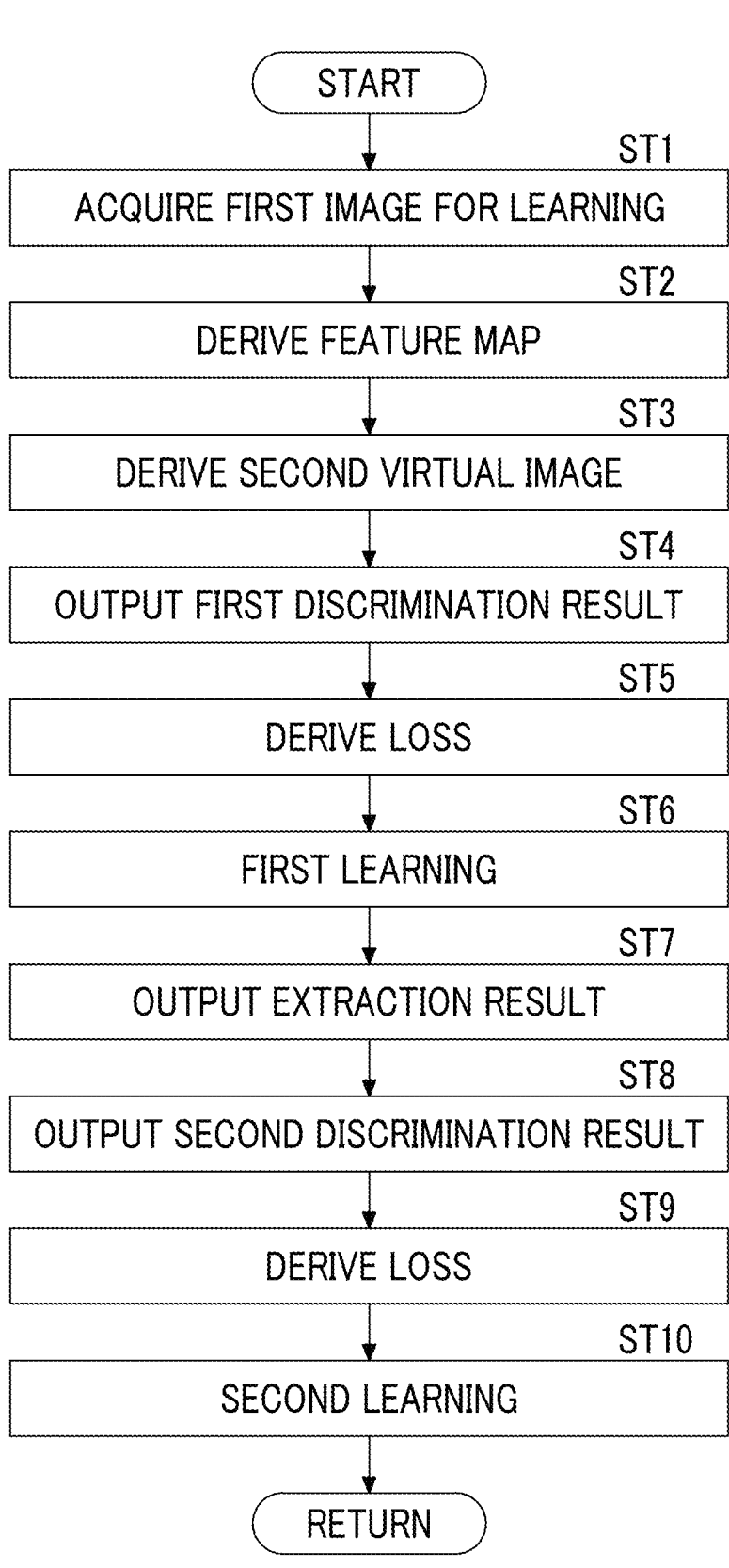
FIG. 9 is a flowchart showing learning processing performed in the first embodiment.

Next, processing performed in the first embodiment will be described. FIG. 9 is a flowchart showing learning processing performed in the first embodiment. It is assumed that the first image GR1 for learning and the ground-truth mask M1 in a case of the presence of a ground-truth mask are acquired from the image storage server 3 by the information acquisition unit 21 and are stored on the storage 13. First, the learning unit 22 acquires the first image GR1 for learning stored on the storage 13 (Step ST1). The learning unit 22 makes the encoder 31 derive the feature map F1 in response to the input of the first image GR1 (Step ST2). Further, the learning unit 22 makes the first decoder 32 derive the second virtual image GV2 in response to the input of the feature map F1 and the information TD2 on the second representation format (Step ST3). Then, the learning unit 22 makes the first discriminator 33 output the discrimination result RF1 and the discrimination result DC1, which are a first discrimination result, in response to the input of the second image GR2 or the second virtual image GV2 (output of the first discrimination result, Step ST4).

Next, the learning unit 22 derives the first loss L1 and the second loss L2 on the basis of the first discrimination result. Further, the learning unit 22 makes the encoder 31 derive the feature map of the second virtual image GV2 in response to the input of the second virtual image GV2, and makes the first decoder 32 output the first virtual image GV1 in response to the input of the feature map of the second virtual image GV2. Then, the learning unit 22 derives the third loss L3 from the first image GR1 and the first virtual image GV1 (loss derivation; Step ST5).

Further, the learning unit 22 performs learning of the encoder 31, the first decoder 32, and the first discriminator 33 on the basis of the first loss L1, the second loss L2, and the third loss L3 (first learning, Step ST6).

Meanwhile, the learning unit 22 makes the second decoder 34 output the extraction result PM1 of the region of interest in response to the input of the feature map F1 (Step ST7). Further, the learning unit 22 makes the second discriminator 35 output the second discrimination result RF2 in response to the input of the extraction result PM1 (Step ST8). Then, the learning unit 22 derives the fifth loss L5 on the basis of the second discrimination result RF2. In a case where the first image GR1 has the ground-truth mask M1, the learning unit 22 derives the fourth loss L4 (loss derivation; Step ST9).

Further, the learning unit 22 performs learning of the encoder 31, the second decoder 34, and the second discriminator 35 on the basis of the fourth loss L4 (if any) and the fifth loss L5 (second learning, Step ST10). Then, the process returns to Step ST1, a next first image GR1 for learning is acquired from the storage 13, and the processing of Steps ST1 to ST10 is repeated. As a result, the extraction model 30 that has been learned is constructed. The processing of Steps ST3 to ST6 and the processing of Steps ST7 to ST10 may be performed in parallel, and the processing of Steps ST7 to ST10 may be performed before the processing of Steps ST3 to ST6.

The learning unit 22 repeats learning until the various losses L1 to L5 become a predetermined threshold value or less, but may repeat learning a predetermined number of times.

Figure 10:
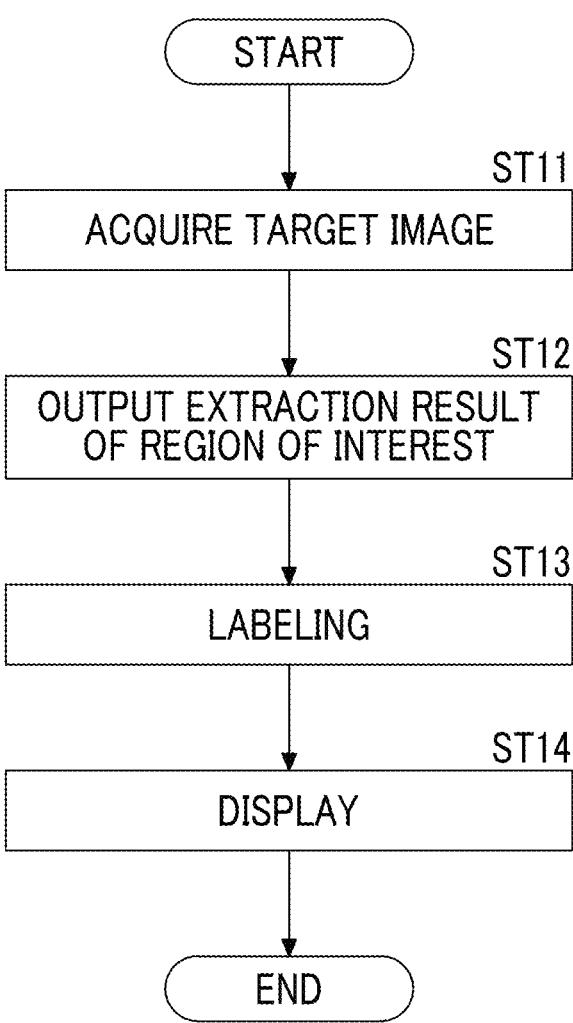
FIG. 10 is a flowchart showing region-of-interest extraction processing performed in the first embodiment.

Next, region-of-interest extraction processing performed in the first embodiment will be described. FIG. 10 is a flowchart of region-of-interest extraction processing performed in the first embodiment. The information acquisition unit 21 acquires the target image (Step ST11), and the extraction unit 23 outputs the extraction result of the region of interest included in the target image (Step ST12). Next, the labeling unit 24 performs labeling 52 of the region of interest included in the target image 51 on the basis of the extraction result of the region of interest (Step ST13). Then, the display control unit 25 displays the labeled target image on the display unit 14 (Step ST14), and the processing ends.

As described above, in the present embodiment, the representation format of the input image and whether the input image is a real image or a virtual image generated by the first decoder 32 are discriminated, and the first discrimination result is output. Further, whether the extraction result PMI of the region of interest by the second decoder 34 is the extraction result of the first image with the ground-truth mask or the extraction result of a first image without the ground-truth mask is discriminated, and the second discrimination result is output. Then, learning of the encoder 31, the first decoder 32, and the first discriminator 33 is performed on the basis of the first discrimination result, and learning of the encoder 31, the second decoder 34, and the second discriminator 35 is performed on the basis of the second discrimination result.

Therefore, as the learning progresses as described above, the encoder 31 and the first decoder 32, and the first discriminator 33 improve the accuracy thereof with each other, and the first discriminator 33 can more accurately discriminate a real image or a virtual image even in a case where an image of any representation format is input. Further, the encoder 31 and the first decoder 32 can generate a virtual image closer to a genuine representation format image, which is not discriminated by the first discriminator 33. Further, the encoder 31 and the first decoder 32, and the first discriminator 33 improve the accuracy thereof with each other, and the second discriminator 35 can more accurately discriminate whether the input image has the ground-truth mask or no ground-truth mask. Furthermore, the encoder 31 and the second decoder 34 can output the more accurate extraction result of the region of interest, in which the presence or absence of the ground-truth mask is not discriminated by the second discriminator 35, regardless of the image with or without the ground-truth mask.

Therefore, the learned extraction model 40 having the learned encoder 31 and second decoder 34 is used to make it possible to extract a region of interest included in a target image regardless of the representation format of the target image, without preparation of a model for each representation format as in the method described in Judy Hoffman, Eric Tseng, Taesung Park, Jun-Yan Zhu, Phillip Isola, Kate Saenko, Alexei A. Efros, Trevor Darrell "CyCADA: Cycle-Consistent Adversarial Domain Adaptation", arXiv: 1711.03213 and without an input of the domain labels at the time of extraction as in the method described in Yunjey Choi, Minje Choi, Munyoung Kim, Jung-Woo Ha, Sunghun Kim, Jaegul Choo "StarGAN: Unified Generative Adversarial Networks for Multi-Domain Image-to-Image Translation", arXiv: 1711.09020.

Figure 11:
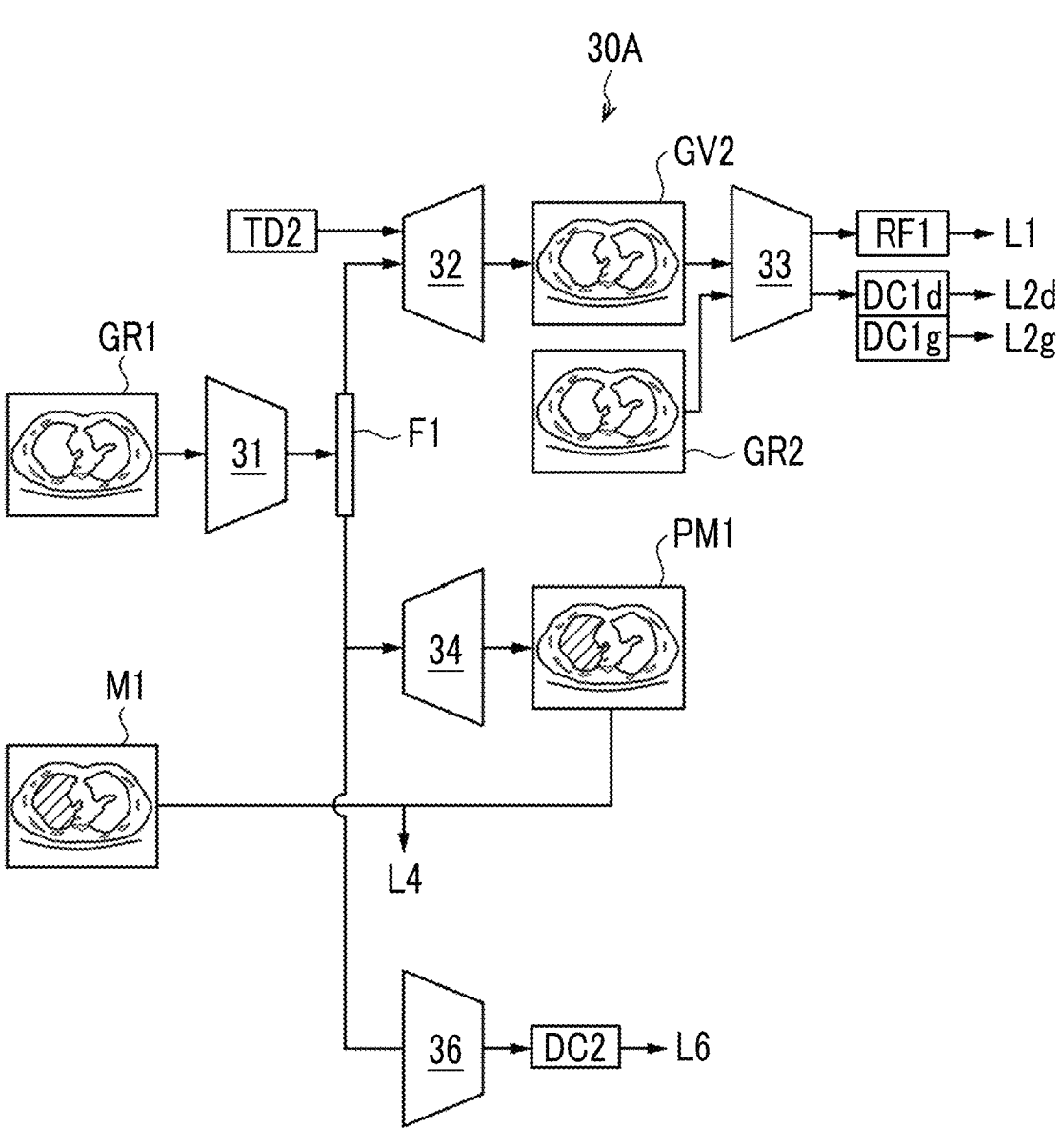
FIG. 11 is a schematic block diagram showing a configuration of an extraction model according to the second embodiment.

Next, a second embodiment of the present disclosure will be described. FIG. 11 is a schematic block diagram showing a configuration of an extraction model according to the second embodiment. In FIG. 11, the same reference numerals are assigned to the same configurations as those in FIG. 3, and detailed description thereof will be omitted. The second embodiment is different from the first embodiment in that an extraction model 30A in the second embodiment comprises a third discriminator 36 instead of the second discriminator 35. In the second embodiment, the encoder 31 and the third discriminator 36 constitute GAN. Since learning of the first decoder 32, the first discriminator 33, and the second decoder 34 is the same as that of the first embodiment, detailed description thereof will be omitted here.

The third discriminator 36 consists of, for example, a convolutional neural network, and discriminates the representation format of the input image on the basis of the feature map output by the encoder 31, and outputs a third discrimination result DC2. That is, as shown in FIG. 11, the third discriminator 36 determines the representation format of the first image GR1 from the feature map F1, which is derived by the encoder 31, and outputs the third discrimination result DC2. For example, in a case where the representation format of the input image is a CT image, if the third discriminator 36 discriminates a CT image, the third discrimination result DC2 is correct, and if the third discriminator 36 discriminates an image other than the CT image, the third discrimination result DC2 is incorrect. Further, in a case where the representation format of the input image is a T2-weighted image, if the third discrimination result DC2 is a T2-weighted image, the third discrimination result DC2 is correct, and if the third discrimination result DC2 is a CT image or T1-weighted image other than the T2-weighted image, the third discrimination result DC2 is incorrect. The learning unit 22 derives a loss on the basis of the output of the third discriminator 36 with regard to the third discrimination result DC2. The loss is referred to as a classification loss. In the present embodiment, the classification loss is denoted by a sixth loss L6.

In the second embodiment, the learning unit 22 performs learning of the third discriminator 36 so that the third discriminator 36 correctly discriminates the third discrimination result DC2 on the representation format of the input image. Further, the learning unit 22 performs learning of the encoder 31 so that the encoder 31 derives the feature map F1 from which the third discriminator 36 incorrectly discriminates the third. discrimination result DC2. That is, learning of the encoder 31 and the third discriminator 36 is performed so that the first loss L1 and the sixth loss L6 are minimized. Specifically, learning of the encoder 31 and the third discriminator 36 is performed so that L1+L6 is a predetermined threshold value or less.

As the learning progresses, the encoder 31 and the third discriminator 36 improve the accuracy thereof with each other, and the third discriminator 36 can more accurately discriminate the representation format no matter what kind of image is input. On the other hand, the encoder 31 can generate the same feature map F1 regardless of the representation format, which is not discriminated by the third discriminator 36, no matter what kind of image is input. Further, as a result, the second decoder 34 can extract the region of interest regardless of the representation format of the image input to the extraction model 30A.

As described above, in the second embodiment, the representation format of the input image and whether the input image is a real image or a virtual image generated by the first decoder 32 are discriminated and the first discrimination result is output, and the representation format of the input image is discriminated on the basis of the feature map F1 derived by the encoder 31 and the third discrimination result is output. Then, learning of the encoder 31, the first decoder 32, and the first discriminator 33 is performed on the basis of the first discrimination result, and learning of the encoder 31 and the third discriminator 36 is performed on the basis of the third discrimination result. Therefore, as in the first embodiment, the region of interest included in the target image can be extracted regardless of the representation format of the target image.

Figure 12:
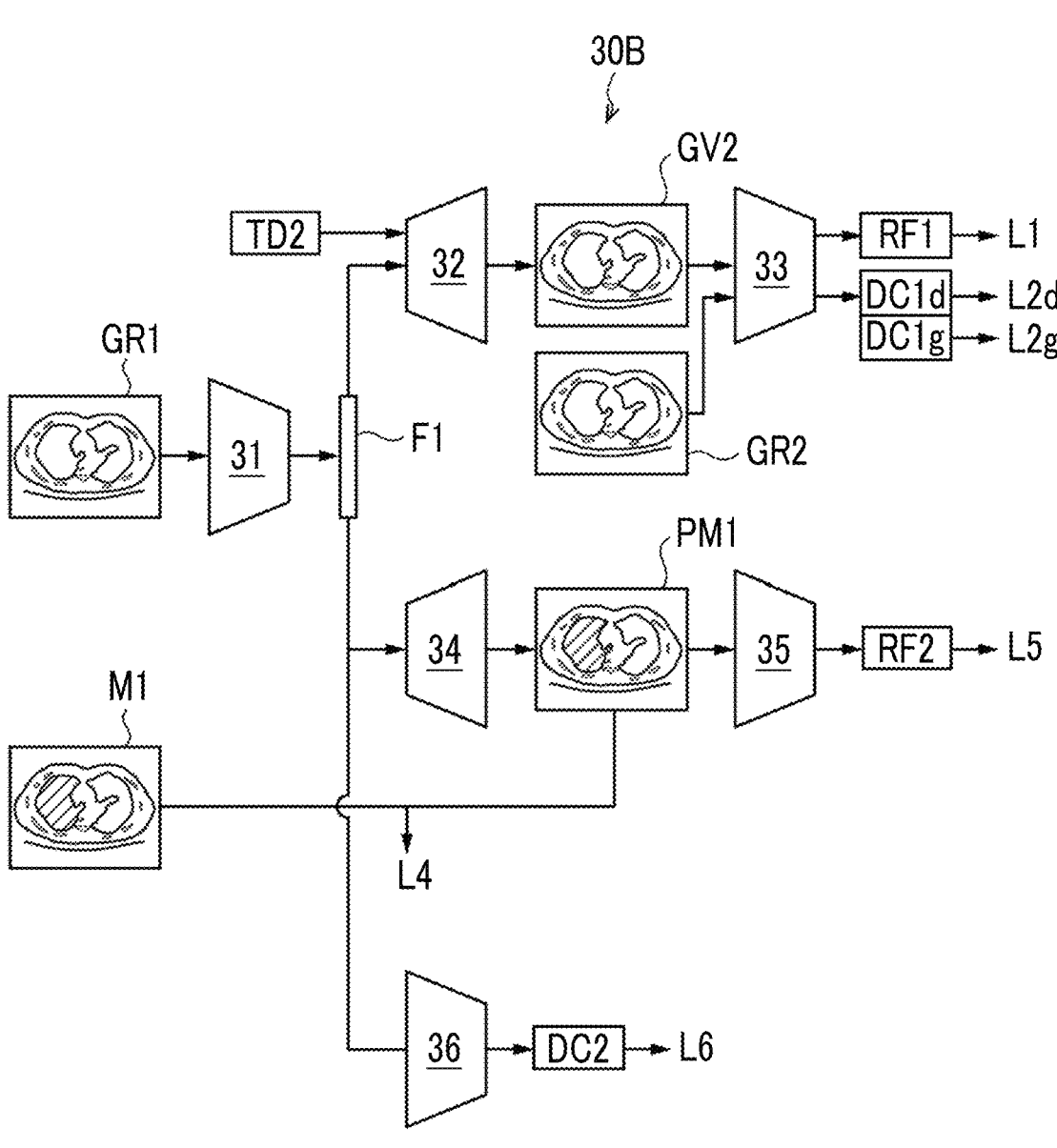
FIG. 12 is a schematic block diagram showing a configuration of an extraction model according to a third embodiment.

In the first embodiment, as in an extraction model 30B shown in FIG. 12, the third discriminator 36 may be provided without omitting the second discriminator 35.

Here, also in the second embodiment, the encoder 31 and the second decoder 34 included in the extraction models 30A and 30B that have been learned are used as the learned extraction model 40.

Further, in each of the above-described embodiments, the region of interest is extracted. from the three-dimensional image of the abdomen of the human body, but the present disclosure is not limited thereto. The technique of the present disclosure can be applied to extraction of a region of interest from a simple X-ray image, an ultrasound image, or the like, in addition to a three-dimensional image such as a CT image or an MRI image.

Further, in each of the above-described embodiments, the T1-weighted image and the T2-weighted image are used as an MRI image, but the present disclosure is not limited thereto. As the MRI image, at least one representation format of a T1-weighted image, a T2-weighted image, a diffusion-weighted image, a FLAIR image, a T1-weighted image before contrast enhancement, or a T1-weighted image after contrast enhancement may be included.

Further, in each of the above-described embodiments, the liver is extracted as a region of interest, but the present disclosure is not limited thereto. The techniques of the present disclosure can also be applied to a case where regions of various structures in the human body, such as lungs, heart, kidneys, and brain, are extracted as a region of interest, in addition to the liver.

Further, in the above-described embodiment, for example, as a hardware structure of a processing unit that executes various processing, such as the information acquisition unit 21, the learning unit 22, the extraction unit 23, the labeling unit 24, and the display control unit 25, the following various processors may be used. The various processors include, for example, a programmable logic device (PLD), such as a field programmable gate array (FPGA), which is a processor having a changeable circuit configuration after manufacture, and a dedicated electrical circuit, such as an application specific integrated circuit (ASIC), which is a processor having a dedicated circuit configuration designed to perform specific processing, in addition to the CPU, which is a general-purpose processor that executes software (programs) to function as various processing units, as described above.

One processing unit may be constituted of one of the various processors or may be constituted of a combination of two or more processors of the same type or different types (for example, a combination of a plurality of FPGAs and a combination of a CPU and an FPGA). Further, the plurality of processing units may constitute one processor.

A first example of the configuration in which the plurality of processing units are constituted of one processor is an aspect in which one or more CPUs and software are combined to constitute one processor and the processor functions as a plurality of processing units. A representative example of the aspect is a computer such as a client and server. A second example of the configuration is an aspect in which a processor that implements all of the functions of a system including the plurality of processing units with one integrated circuit (IC) chip is used. A representative example of the aspect is a system on chip (SoC). As described above, as the hardware structure of various processing units, one or more of the various processors are used.

Furthermore, as the hardware structure of the various processors, more specifically, an electrical circuit (circuitry) in which circuit elements, such as semiconductor elements, are combined may be used

What is claimed is:

1. A learning apparatus of an extraction model that extracts a region of interest from images having a plurality of different representation formats comprising at least one processor, wherein the extraction model has an encoder that extracts a feature amount of a first image of a first representation format to derive a feature map of the first image, a first decoder that derives a second virtual image of a second representation format different from the first representation format of the first image on the basis of the feature map, a first discriminator that discriminates a representation format of an input image and whether the input image is a real image or a virtual image generated by the first decoder, and outputs a first discrimination result, a second decoder that extracts a region of interest of the first image on the basis of the feature map, and a second discriminator that discriminates whether an extraction result of the region of interest by the second decoder is an extraction result of a first image with a ground-truth mask or an extraction result of a first image without the ground-truth mask, and outputs a second discrimination result, wherein the extraction model further comprises a second instance of the first decoder configured to derive a third virtual image of a third representation format which is different from the first representation format of the first image and the second representation format of the second virtual image, and wherein the processor is configured to perform learning of the encoder, the first decoder, and the first discriminator on the basis of the first discrimination result, and that performs learning of the encoder, the second decoder, and the second discriminator on the basis of the second discrimination result, wherein the learning of the second discriminator is performed by alternatively inputting the first image with the ground-truth mask and the first image without the ground-truth mask.

2. The learning apparatus according to claim 1,
wherein the processor is configured to make the encoder
derive a feature map of the second virtual image in
response to an input of the second virtual image,
makes the first decoder derive a first virtual image of
the first representation format on the basis of the
feature map of the second virtual image, and
performs learning of the encoder, the first decoder, and
the first discriminator on the basis of a difference
between the first image of the first representation
format and the first virtual image.

3. The learning apparatus according to claim 1,
wherein in a case where the first image has the ground-
truth mask for the region of interest, the processor is
configured to perform learning of the second decoder
on the basis of the extraction result of the region of
interest and the ground-truth mask.

4. The learning apparatus according to claim 1,
wherein the extraction model further has a third discrimi-
nator that discriminates a representation format of the
first image of the first representation format that is input
to the encoder on the basis of the feature map, and that
outputs a third discrimination result, and
the processor is configured to perform learning of the
encoder and the third discriminator on the basis of the
third discrimination result.

5. The learning apparatus according to claim 1,
wherein the first image of the first representation format
is a three-dimensional medical image, and first the
representation format includes representation formats
of a CT image and an MRI image.

6. The learning apparatus according to claim 5,
wherein the first representation format includes at least
one representation format of a T1-weighted image, a
T2-weighted image, a diffusion-weighted image, a
FLAIR image, a T1-weighted image before contrast
enhancement, or a T1-weighted image after contrast
enhancement, in an MRI image.

7. A region-of-interest extraction apparatus comprising
the at least one processor, and
the encoder and the second decoder in the extraction
model learned by the learning apparatus according to
claim 1,
wherein the at least one processor is configured to extract
a region of interest of an image of any representation
format from the image of any representation format by
the encoder and the second decoder.

8. A learning apparatus of an extraction model that
extracts a region of interest from images having a plurality
of different representation formats comprising at least one
processor,
wherein the extraction model has
an encoder that extracts a feature amount of a first image
of a first representation format to derive a feature map
of the first image,
a first decoder that derives a second virtual image of a
second representation format different from the repre-
sentation format of the first image on the basis of the
feature map,
a first discriminator that discriminates a representation
format of an input image and whether the input image
is a real image or a virtual image generated by the first
decoder, and outputs a first discrimination result,
a second decoder that extracts a region of interest of the
first image on the basis of the feature map, and
a third discriminator that discriminates a representation
format of the first image of the first representation format that is input to the encoder on the basis of the
feature map, and outputs a third discrimination result,
wherein the extraction model further comprises a second
instance of the first decoder configured to derive a third
virtual image of a third representation format which is
different from the first representation format of the first
image and the second representation format of the
second virtual image, and
wherein the processor is configured to perform learning of
the encoder, the first decoder, and the first discriminator
on the basis of the first discrimination result, and that
performs learning of the encoder and the third discrimi-
nator on the basis of the third discrimination result,
wherein the learning of the third discriminator is per-
formed by alternately inputting the first image with a
ground-truth mask and the first image without the
ground-truth mask.

9. The learning apparatus according to claim 8,
wherein the first image of the first representation format
is a three-dimensional medical image, and the first
representation format includes representation formats
of a CT image and an MRI image.

10. The learning apparatus according to claim 9,
wherein the first representation format includes at least
one representation format of a T1-weighted image, a
T2-weighted image, a diffusion-weighted image, a
FLAIR image, a T1-weighted image before contrast
enhancement, or a T1-weighted image after contrast
enhancement, in the MRI image.

11. A region-of-interest extraction apparatus comprising
the at least one processor, and
the encoder and the second decoder in the extraction
model learned by the learning apparatus according to
claim 8,
wherein the at least one processor is configured to extract
a region of interest of an image of any representation
format from the image of any representation format by
the encoder and the second decoder.

12. A learning method of an extraction model that extracts
a region of interest from images having a plurality of
different representation formats,
wherein the extraction model has
an encoder that extracts a feature amount of a first image
of a first representation format to derive a feature map
of the first image,
a first decoder that derives a second virtual image of a
second representation format different from the first
representation format of the first image on the basis of
the feature map,
a first discriminator that discriminates a representation
format of an input image and whether the input image
is a real image or a virtual image generated by the first
decoder, and outputs a first discrimination result,
a second decoder that extracts a region of interest of the
first image on the basis of the feature map, and
a second discriminator that discriminates whether an
extraction result of the region of interest by the second
decoder is an extraction result of a first image with a
ground-truth mask or an extraction result of a first
image without the ground-truth mask, and outputs a
second discrimination result,
wherein the extraction model further comprises a second
instance of the first decoder configured to derive a third
virtual image of a third representation format which is
different from the first representation format of the first
image and the second representation format of the
second virtual image, and the learning method comprises:

performing learning of the encoder, the first decoder, and the first discriminator on the basis of the first discrimination result; and performing learning of the encoder, the second decoder, and the second discriminator on the basis of the second discrimination result, wherein the learning of the second discriminator is performed by alternately inputting the first image with the ground-truth mask and the first image without the ground-truth mask.

13. A region-of-interest extraction method comprising:

extracting a region of interest of an image of any representation format from the image of any representation format by the encoder and the second decoder in the extraction model learned by the learning method according to claim 12.

14. A non-transitory computer-readable storage medium that stores a region-of-interest extraction program causing a computer to execute a process comprising:

extracting a region of interest of an image of any representation format from the image of any representation format by the encoder and the second decoder in the extraction model learned by the learning method according to claim 12.

15. A learning method of an extraction model that extracts a region of interest from images having a plurality of different representation formats, wherein the extraction model has an encoder that extracts a feature amount of a first image of a first representation format to derive a feature map of the first image, a first decoder that derives a second virtual image of a second representation format different from the first representation format of the first image on the basis of the feature map, a first discriminator that discriminates a representation format of an input image and whether the input image is a real image or a virtual image generated by the first decoder, and outputs a first discrimination result, a second decoder that extracts a region of interest of the first image on the basis of the feature map, and a third discriminator that discriminates a representation format of the first image of the first representation format that is input to the encoder on the basis of the feature map, and outputs a third discrimination result, wherein the extraction model further comprises a second instance of the first decoder configured to derive a third virtual image of a third representation format which is different from the first representation format of the first image and the second representation format of the second virtual image, and the learning method comprises:

performing learning of the encoder, the first decoder, and the first discriminator on the basis of the first discrimination result; and performing learning of the encoder and the third discriminator on the basis of the third discrimination result, wherein the learning of the third discriminator is performed by alternately inputting the first image with a ground-truth mask and the first image without the ground-truth mask.

16. A region-of-interest extraction method comprising:

extracting a region of interest of an image of any representation format from the image of any representation format by the encoder and the second decoder in the extraction model learned by the learning method according to claim 15.

17. A non-transitory computer-readable storage medium that stores a region-of-interest extraction program causing a computer to execute a process comprising:

extracting a region of interest of an image of any representation format from the image of any representation format by the encoder and the second decoder in the extraction model learned by the learning method according to claim 15.

18. A non-transitory computer-readable storage medium that stores a learning program causing a computer to execute a learning method of an extraction model that extracts a region of interest from images having a plurality of different representation formats, wherein the extraction model has an encoder that extracts a feature amount of a first image of a first representation format to derive a feature map of the first image, a first decoder that derives a second virtual image of a second representation format different from the first representation format of the first image on the basis of the feature map, a first discriminator that discriminates a representation format of an input image and whether the input image is a real image or a virtual image generated by the first decoder, and outputs a first discrimination result, a second decoder that extracts a region of interest of the first image on the basis of the feature map, and a second discriminator that discriminates whether an extraction result of the region of interest by the second decoder is an extraction result of a first image with a ground-truth mask or an extraction result of a first image without the ground-truth mask, and outputs a second discrimination result, wherein the extraction model further comprises a second instance of the first decoder configured to derive a third virtual image of a third representation format which is different from the first representation format of the first image and the second representation format of the second virtual image, and the learning program causes the computer to execute a process comprising:

performing learning of the encoder, the first decoder, and the first discriminator on the basis of the first discrimination result; and performing learning of the encoder, the second decoder, and the second discriminator on the basis of the second discrimination result, wherein the learning of the second discriminator is performed by alternately inputting the first image with the ground-truth mask and the first image without the ground-truth mask.

19. A non-transitory computer-readable storage medium that stores a learning program causing a computer to execute a learning method of an extraction model that extracts a region of interest from images having a plurality of different representation formats, wherein the extraction model has an encoder that extracts a feature amount of a first image of a first representation format to derive a feature map of the first image, a first decoder that derives a second virtual image of a second representation format different from the first representation format of the first image on the basis of the feature map, a first discriminator that discriminates a representation format of an input image and whether the input image is a real image or a virtual image generated by the first decoder, and outputs a first discrimination result, a second decoder that extracts a region of interest of the first image on the basis of the feature map, and a third discriminator that discriminates a representation format of the first image of the first representation format that is input to the encoder on the basis of the feature map, and outputs a third discrimination result, wherein the extraction model further comprises a second instance of the first decoder configured to derive a third virtual image of a third representation format which is different from the first representation format of the first image and the second representation format of the second virtual image, and the learning program causes the computer to execute a process comprising:

performing learning of the encoder, the first decoder, and the first discriminator on the basis of the first discrimination result; and performing learning of the encoder and the third discriminator on the basis of the third discrimination result, wherein the learning of the third discriminator is performed by alternately inputting the first image with a ground-truth mask and the first image without the ground-truth mask.

* * * * *